(12) United States Patent
Llop et al.

(10) Patent No.: US 10,307,226 B2
(45) Date of Patent: Jun. 4, 2019

(54) BONE FOUNDATION GUIDE AND METHOD OF USE

(71) Applicant: NATIONAL DENTEX, LLC, Palm Beach Gardens, FL (US)

(72) Inventors: Daniel R. Llop, Reno, NV (US); Armand C. Jusuf, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 465 days.

(21) Appl. No.: 14/214,555

(22) Filed: Mar. 14, 2014

(65) Prior Publication Data

US 2014/0272778 A1 Sep. 18, 2014

Related U.S. Application Data

(60) Provisional application No. 61/784,029, filed on Mar. 14, 2013.

(51) Int. Cl.
*A61C 8/00* (2006.01)
*A61C 1/08* (2006.01)
*A61C 8/02* (2006.01)

(52) U.S. Cl.
CPC ............ *A61C 8/0089* (2013.01); *A61C 1/084* (2013.01); *A61C 8/0006* (2013.01)

(58) Field of Classification Search
CPC ....... A61C 8/005; A61C 13/225; A61C 13/10; A61C 13/26; A61C 1/082; A61C 1/084;
(Continued)

(56) References Cited

U.S. PATENT DOCUMENTS 5,018,970 A 5/1991 Stordahl
5,725,376 A 3/1998 Poirier
(Continued)

FOREIGN PATENT DOCUMENTS

CA 2795668 A1 11/2011
CA 2934371 A1 6/2015
(Continued)

OTHER PUBLICATIONS

Website showing a bone reduction guide that was uploaded by www.dentalinformation.com in Aug. 4, 2011 located at https://www.youtube.com/watch?v=AZnReFZmLN8 the upload is entitled Bone Reduction and Bone Supported Guide for Guided Dental Implant Surgery.
(Continued)

*Primary Examiner* — Heidi M Eide
*Assistant Examiner* — Mirayda A Aponte
(74) *Attorney, Agent, or Firm* — Frost Brown Todd LLC

(57) ABSTRACT

The disclosure relates, in some embodiments, to a bone foundation guide configured to guide alteration of an alveolar ridge. A bone foundation guide may include a body with (a) a first end of a buccal wall and a first end of a lingual wall each connected to a first end of the body and (b) a second end of the buccal wall and a second end of the lingual wall each connected to a second end of the body such that the buccal wall is substantially parallel to the lingual wall and a space between the buccal wall and the lingual wall defines an open surgical space. A body may be configured to sit adjacent to a tissue spacing gasket having a thickness equivalent to a gum tissue that would normally cover the bone segment.

14 Claims, 5 Drawing Sheets

(58) Field of Classification Search
CPC ... A61C 5/023; A61C 8/0048; A61C 13/2656; A61C 13/0001; A61C 13/0062; A61C 13/0089; A61C 13/0004
USPC ....... 433/167–176, 201.1, 199.1, 200.1, 181, 433/182, 75; 264/16–20
See application file for complete search history.

(56) References Cited

U.S. PATENT DOCUMENTS

| | | | |
|---|---|---|---|
| 5,967,777 | A | 10/1999 | Klein et al. |
| 6,319,006 | B1 | 11/2001 | Scherer et al. |
| 6,382,975 | B1 | 5/2002 | Poirier |
| 6,491,696 | B1 | 12/2002 | Kunkel |
| 6,672,870 | B2 | 1/2004 | Knapp |
| 6,814,575 | B2 | 11/2004 | Poirier |
| 6,997,707 | B2 | 2/2006 | Germanier |
| 7,331,786 | B2 | 2/2008 | Poirier |
| 7,632,097 | B2 | 12/2009 | De Clerck |
| 7,774,084 | B2 | 8/2010 | Cinader, Jr. |
| 7,824,181 | B2 | 11/2010 | Sers |
| 7,866,980 | B2 | 1/2011 | Poirier |
| 7,887,327 | B2 | 2/2011 | Marotta |
| 7,905,726 | B2 | 3/2011 | Stumpel |
| 7,909,606 | B2 | 3/2011 | Marcello |
| 7,942,668 | B2 | 5/2011 | Brajnovic et al. |
| 8,021,153 | B2 | 9/2011 | Poirier |
| 8,038,440 | B2 | 10/2011 | Swaelens et al. |
| 8,135,492 | B2 | 3/2012 | Yau et al. |
| 8,142,189 | B2 | 3/2012 | Brajnovic |
| 8,352,060 | B2 | 1/2013 | Chun et al. |
| 8,364,301 | B2 | 1/2013 | Schmitt |
| 8,371,849 | B2 | 2/2013 | Gao |
| 8,529,255 | B2 | 9/2013 | Poirier et al. |
| 8,540,510 | B2 | 9/2013 | Brajnovic |
| 8,574,302 | B2 | 11/2013 | McKay |
| 8,585,402 | B2 | 11/2013 | Vogel et al. |
| 8,706,672 | B2 | 4/2014 | Malfliet et al. |
| 8,770,972 | B2 | 7/2014 | Swaelens et al. |
| 8,777,612 | B2 | 7/2014 | Suttin et al. |
| 8,827,699 | B2 | 9/2014 | Bavar |
| 8,899,984 | B2 | 12/2014 | Llop et al. |
| 9,069,914 | B2 | 6/2015 | Kopelman et al. |
| 9,107,723 | B2 | 8/2015 | Hall et al. |
| 9,155,548 | B2 | 10/2015 | Lin |
| 9,155,599 | B2 | 10/2015 | Thompson et al. |
| 9,161,822 | B2 | 10/2015 | Stevens et al. |
| 9,168,112 | B2 | 10/2015 | Haber |
| 9,173,723 | B2 | 11/2015 | Harrison |
| 9,211,165 | B2 | 12/2015 | Jamison |
| 9,226,801 | B2 | 1/2016 | Groscurth et al. |
| 9,259,291 | B2 | 2/2016 | Gantes |
| 9,308,055 | B2 | 4/2016 | Fisker et al. |
| 9,336,336 | B2 | 5/2016 | Deichmann et al. |
| 9,358,082 | B2 | 6/2016 | Nilsson |
| 9,381,072 | B2 | 7/2016 | Furrer et al. |
| 9,402,698 | B2 | 8/2016 | Thompson et al. |
| 9,498,307 | B2 | 11/2016 | Harrison |
| 2006/0166169 | A1 | 7/2006 | Dawood |
| 2007/0162014 | A1* | 7/2007 | Campbell ............ A61B 17/663 606/285 |
| 2009/0092948 | A1 | 4/2009 | Gantes |
| 2009/0263764 | A1* | 10/2009 | Berckmans, III ...... A61C 1/084 433/215 |
| 2009/0274990 | A1 | 11/2009 | Kim |
| 2009/0298008 | A1 | 12/2009 | Groscurth et al. |
| 2010/0035201 | A1* | 2/2010 | Beck .................... A61C 1/084 433/76 |
| 2010/0055640 | A1* | 3/2010 | Van Lierde ............ A61C 1/084 433/72 |
| 2010/0124731 | A1 | 5/2010 | Groscurth et al. |
| 2010/0316974 | A1 | 12/2010 | Yau et al. |
| 2011/0033819 | A1 | 2/2011 | Freyer et al. |
| 2011/0045431 | A1 | 2/2011 | Groscurth et al. |
| 2011/0045432 | A1 | 2/2011 | Groscurth et al. |
| 2011/0111371 | A1 | 5/2011 | Haber |
| 2011/0151399 | A1 | 6/2011 | De Clerck et al. |
| 2011/0207084 | A1* | 8/2011 | Kaigler, Sr. .......... A61B 17/663 433/174 |
| 2011/0256508 | A1 | 10/2011 | Gantes |
| 2012/0046914 | A1 | 2/2012 | Gao |
| 2012/0053593 | A1 | 3/2012 | Abboud |
| 2012/0156638 | A1 | 6/2012 | Gantes |
| 2012/0261848 | A1 | 10/2012 | Haraszati |
| 2012/0277899 | A1 | 11/2012 | Chun et al. |
| 2013/0011813 | A1 | 1/2013 | Garcia et al. |
| 2013/0023888 | A1 | 1/2013 | Choi et al. |
| 2013/0071811 | A1* | 3/2013 | Groscurth ............ A61C 1/084 433/75 |
| 2013/0209956 | A1 | 8/2013 | Sanders |
| 2013/0216974 | A1* | 8/2013 | Schmalzle ............ A61C 1/082 433/75 |
| 2013/0252202 | A1 | 9/2013 | Pardeller et al. |
| 2014/0026419 | A1 | 1/2014 | Haber |
| 2014/0080086 | A1 | 3/2014 | Chen |
| 2014/0080092 | A1 | 3/2014 | Suttin et al. |
| 2014/0099599 | A1 | 4/2014 | Harrison et al. |
| 2014/0255873 | A1 | 9/2014 | Bullis et al. |
| 2014/0255876 | A1 | 9/2014 | Alpern et al. |
| 2014/0272779 | A1 | 9/2014 | Okay |
| 2014/0272780 | A1 | 9/2014 | Llop |
| 2015/0010881 | A1 | 1/2015 | Llop |
| 2015/0025855 | A1 | 1/2015 | Fisker et al. |
| 2015/0030995 | A1 | 1/2015 | Villa |
| 2015/0037756 | A1 | 2/2015 | Berckmans, III et al. |
| 2015/0093717 | A1 | 4/2015 | Ali |
| 2015/0111179 | A1 | 4/2015 | Suttin |
| 2015/0133956 | A1 | 5/2015 | Dayan et al. |
| 2015/0150684 | A1 | 6/2015 | De Clerck |
| 2015/0230894 | A1 | 8/2015 | Juzbasic et al. |
| 2015/0265372 | A1 | 9/2015 | Kim et al. |
| 2015/0272704 | A1 | 10/2015 | Watson et al. |
| 2015/0272705 | A1 | 10/2015 | Watson et al. |
| 2015/0302170 | A1 | 10/2015 | Berckmans, III et al. |
| 2015/0351866 | A1* | 12/2015 | Thompson, Jr. ....... A61C 1/084 433/173 |
| 2015/0359614 | A1 | 12/2015 | Sachdeva et al. |
| 2015/0374460 | A1 | 12/2015 | Sachdeva et al. |
| 2016/0008110 | A1 | 1/2016 | Harrison |
| 2016/0038255 | A1 | 2/2016 | Llop |
| 2016/0106517 | A1 | 4/2016 | Groscurth et al. |
| 2016/0106518 | A1 | 4/2016 | Choi et al. |
| 2016/0128810 | A1 | 5/2016 | Fostick et al. |
| 2016/0157967 | A1 | 6/2016 | Kim et al. |
| 2016/0157970 | A1 | 6/2016 | Gantes |
| 2016/0278878 | A1 | 9/2016 | Watson et al. |
| 2016/0287336 | A1 | 10/2016 | Kim et al. |
| 2016/0324599 | A1 | 11/2016 | Harrison |
| 2016/0045280 | A1 | 12/2016 | Haber |
| 2017/0071697 | A1 | 3/2017 | Groscurth et al. |
| 2017/0112591 | A1 | 4/2017 | Llop |
| 2017/0112592 | A1 | 4/2017 | Groscurth et al. |
| 2017/0252126 | A1 | 9/2017 | Llop |

FOREIGN PATENT DOCUMENTS

| | | | |
|---|---|---|---|
| EP | 2 425 797 A1 | 3/2012 | |
| MX | 2014001163 A | 7/2015 | |
| WO | WO 2010/061391 | 6/2010 | |
| WO | WO 2012/007615 | 1/2012 | |
| WO | WO-2013181721 A2 * | 12/2013 | ........... A61F 2/2803 |
| WO | WO 2014/130536 | 8/2014 | |
| WO | WO2015148891 A3 | 10/2015 | |

OTHER PUBLICATIONS

Select pages showing a bone reduction guide from the publication Art of Computer Guided Implantology by Tradiev and Rosenfield Copyright 2009.
International Search Report and Written Opinion dated Dec. 28, 2017 for Application No. PCT/US2017/054804, 10 pgs.
Online video of zygomatic dental implant surgery: http://www.

(56) References Cited

OTHER PUBLICATIONS youtube.com/watch?v=TGBxbP9aa2g&sns=em Title Zygomatic Implant Guided Surgery—Noris Medical, Published on Mar. 11, 2015, 1 pg.

Select pages showing a bone reduction guide from the publication Art of Computer Guided Implantology by Tradiev and Rosenfield, Copyright 2009, 3 pgs.

Website showing a bone reduction guide that was uploaded by www.dentalinformation.com on Aug. 4, 2011 located at https://www.youtube.com/watch?v=AZnReFZmLN8 the upload is entitled Bone Reduction and Bone Supported Guide for Guided Dental Implant Surgery, 1 pg.

International Search Report and Written Opinion dated Mar. 2, 2016 for Application No. PCT/US2015/061002, 14 pgs.

International Search Report and Written Opinion dated Jul. 26, 2016 for Application No. PCT/US2016/021097, 13 pgs.

International Search Report and Written Opinion dated Jun. 16, 2017 for Application No. PCT/US2017/020746, 13 pgs.

\* cited by examiner

BONE FOUNDATION GUIDE AND METHOD OF USE

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to bone foundation guides. More particularity to those bone foundation guides that could incorporate dental implant surgical guide capabilities.

BACKGROUND

As a person ages, they generally incur tooth and bone loss requiring prosthetic replacement as provided by the dental profession. One of the more important aspects of this replacement procedure is the need to solidly anchor within the available bone structure those implants used to secure individual (replacement artificial tooth) or collective (e.g., denture) dental prosthetic. When teeth lose bone around their roots, the bone (e.g., mandibular arch or the maxillary arch) may become uneven (either thinned out or too bulky) in various places in the respective dental arch. This bone condition may make the dental restorative process in that particular area more difficult than when such bone loss has not occurred. It could be thought as building a house/foundation on an unleveled/uneven ground.

In order for the dental prosthetic (or restoration) to be properly fitted to the patient in a substantially esthetically and functionally acceptable position, the dental health care professional (e.g. dental surgeon) may first have to alter the bone of the dental surgical site (especially in those situations where the dental prosthetic is redressing significant tooth loss). This corrective process could start by making one or more incisions in gum area that otherwise designates the dental surgical or restoration site. These incisions substantially allow the gum tissue to be peeled back to expose the bone at the dental surgical site. The dental surgeon, in order to generally make dental surgical site/dental arch symmetrical in all relevant dimensions for the dental restoration (e.g., removable denture) or implant sites (e.g. fixed prosthetics), may then apply one or more cutting tools to generally reduce or remove unwanted high points or thickened places on the exposed bone structure. In other instances, the dental surgeon may add bone material to the exposed bone structure to further fill out the arch's profile or otherwise strengthen its structure.

During this process, the dental surgeon could bring the top portion of the alveolar ridge (e.g., one of the two jaw ridges either on the roof of the mouth or the bottom of the mouth that contain the sockets or alveoli of the teeth) to the correct surgical dimensions ("leveling out") by utilizing a bone foundation guide generally placed upon and secured to the bone structure to guide the cutting/augmenting of the exposed bone. The bone foundation guide solves the problem of "estimating" the vertical height and width of the bone at the "coronal" level by guiding the surgeon's operation of the cutting tools and/or augmentation of the bone. This allows subsequent and accurate placement of the dental implants and respective prosthetics at the proper patient-specific vertical and horizontal levels. This bone adjustment process may also provide for the creation of the proper inter-occlusal room (e.g., the space that exists between the opposing teeth and the open tissue (e.g., that will receive the dental prosthetic) to generally insure that proper jaw operation and alignment, smile line and phonetics occur when the dental prosthetic is finally located within the patient's mouth.

After the exposed bone has been properly been prepared (e.g., reduced/augmented), the bone foundation guide may be removed. A dental implant surgical guide may be subsequently fitted and attached in its place at the remodeled bone of dental surgical site. The dental implant surgical guide may be used to guide the operation of implant accessories needed to prepare the dental surgical site to receive the dental implants. The dental implant surgical guide may then be used to suitably locate the dental implants into the prepared bone structure. After the dental implants are properly located, the dental implant surgical guide may be removed and healing abutments (if required) may be fitted to the dental implants to create a space in the reattached gum proximate to the dental implant(s) that receives a portion (e.g., the base) of prosthetic (e.g., tooth). Once the healing abutments are attached, the gum tissue may sutured back up sand around the dental implant/healing abutment.

As needed, a full upper or full lower denture/tooth may be fitted to the implants either at the close of the dental surgery or later after healing of the tissues/osseo-integration of bone to implant(s) has occurred. Once the healing/osseo-integration has finalized, the dental surgeon could remove the healing abutments to open up the space proximate to the implants that receives the base of the prosthetic to place and affix the dental prosthetic securely to the implant(s).

The bone foundation guide and the implant dental surgical guide for the implants are generally considered separate instruments that are generally designed, manufactured and used independently of one another other. The design and creation of these guides can be accomplished through digital dentistry (e.g., pre-surgical digital methods and associated apparatuses to obtain and merge medical imaging information taken from the patient's mouth and/or dental castings of the patient's mouth to create a patient-specific virtual models of the preoperative and post-operative mouth and a surgical plan connecting the two models) or manually by dental art and hand (e.g., analogue dental design and preparation).

This separation or compartmentalization of dental guide capabilities could result in higher costs, manpower, and surgical time that could be found than if the two dental guides could be combined into one multipurpose device. The use of such a combination dental appliance could accordingly lead to an increase in the affordability of such dental procedures and results.

What could be needed is a bone foundation guide-dental implant surgical guide combination wherein the dental implant surgical guide directly and reversibly attaches to the bone foundation guide in situ after the open bone at the surgical site has been properly reduced/augmented using the bone foundation guide. The dental implant surgical guide, by attaching directly to or through the bone foundation guide as anchored, could utilize the bone foundation guide as a base to generally position the dental implant/implant accessories through the open surgical space to provide proper implant placement relative to the patient's dental surgical site.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide an dental implant surgical guide that is reversibly combines with bone foundation guide to consequentially properly place a dental implant-retained prosthesis in a manner that reduces patient stress and bruising that may occur if the two guides were applied separately;

the ability to use a digital virtual model of patent mouth to design a bone foundation guide and a dental implant surgical guide to consequentially conjoin both guides to properly locate a surgical attachment that locates and secures a fixed prosthetic;

to provide dental implant surgical guide/bone foundation guide combination to reduce cost, time and man-hours needed in a surgical procedure to properly locate and attach a fixed prosthetic to a dental surgical site;

the ability to use digital dentistry to control the design and manufacture of a dental implant surgical guide/a bone foundation guide combination to digitally control refine the accuracy of the bone foundation guide; dental implant surgical guide; and final fixed prosthetic; and to provide a tissue spacing guide that can working in conjunction with combined bone foundation guide/dental implant surgical guide to adjust for the height of gum tissue that would normally cover the bone at the dental surgical site;

the ability to design and manufacture a dental surgical guide, bone foundation guide, and tissue spacing gasket to allow them to mate together and allow implant appliances and implants to pass through the combination onto the bone at a dental surgical site.

to provide a dental surgical guide, bone foundation guide, and tissue spacing gasket to have matching contours and aligned openings and apertures that allow guides and gasket to be combined into one operating unit to properly locate and attach a fixed prosthetic to a dental surgical site.

These and other advantages may be realized by reference to the remaining portions of the specification, claims, and abstract.

Brief Description of One Embodiment of the Present Invention

One possible embodiment of the invention could be a bone foundation guide comprising a body having a buccal wall and a lingual wall that is continuously connected by a first end and second end forming an open surgical space between the ends that connects a top of the body with a bottom of the body, wherein the bottom is further contoured to receive and rest upon at least a portion of a bone segment of a respective patient's alveolar ridge to guide the surgical alteration of a respective patient's alveolar ridge while the top is further contoured to reversibly receive and support a bottom portion of a dental implant surgical guide.

Yet another embodiment of the invention could be a combination of a bone foundation guide and a dental implant surgical guide comprising a bone foundation guide having a buccal wall and a lingual wall held apart from one another by a first end and second end to further create an open surgical space connecting a top of the body with a bottom of the body, the bottom is further contoured to receive and rest upon at least a portion of a bone segment of a respective patient's alveolar ridge; a dental implant surgical guide bone segment having a body with a top and a bottom and having one or more apertures to guide the drilling for and the passage of one or more dental implants; wherein the top and the bottom portion fit together to allow the dental implant surgical guide to rest upon to the bone foundation guide.

Still yet another embodiment of the invention could be a combination of a bone foundation guide, a dental implant surgical guide, and a tissue spacing gasket comprising a bone foundation guide having a buccal wall and a lingual wall held apart from one another by a first end and second end to further create an open surgical space connecting a top and a bottom, the bottom is further contoured to receive and rest upon at least a portion of a bone segment of a respective patient's alveolar ridge while the top is further contoured to removably receive and support a dental implant surgical guide; the dental implant surgical guide having a body with one or more apertures to locate one or more implants to the respective patient's alveolar ridge; wherein the bone foundation guide and receives the bottom portion; the tissue spacing gasket is placed between the bottom of the bone foundation guide and the respective patient's alveolar ridge to replicate the depth of tissue as removed from the respective patient's alveolar ridge, tissue spacing gasket further having gasket apertures that may align with apertures of the dental implant surgical guide apertures.

Still another possible embodiment of the invention could be a method of using a bone foundation guide in combination with a surgical dental guide, comprising the following steps, providing a bone foundation guide having top and bottom that are connected by an open surgical space, the bottom being further contoured to receive and rest upon at least a portion of a bone segment of a respective patient's alveolar ridge to guide the alteration of a respective patient's alveolar ridge while the top is further contoured to reversibly receive and support a dental implant surgical guide; providing a dental implant surgical guide having body penetrated by one or more implant apertures; anchoring bone foundation guide upon a respective patient's alveolar to alter a portion of the bone of the alveolar ridge of a particular patient; and placing the dental implant guide upon the bone foundation guide.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

Figure 1:
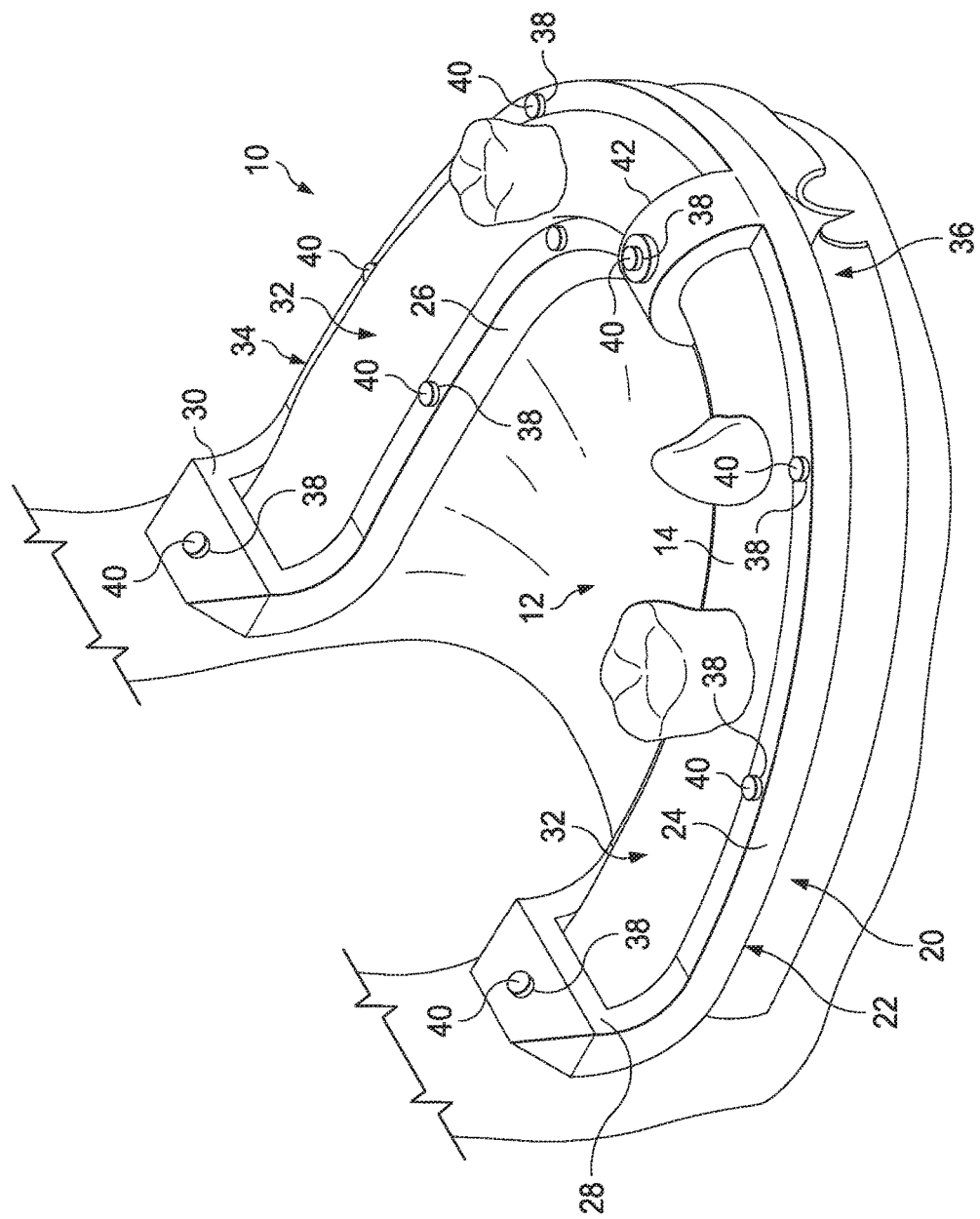
FIG. 1 is substantially a perspective view of one possible embodiment of the bone foundation guide the invention applied to an alveolar ridge.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The present invention 10 could comprise of bone foundation guide 20 that can accommodate and support a dental implant surgical guide 50 and a respective method or process of such use 100. Both the bone foundation guide body 22 and the dental implant surgical guide 50 may be designed and created together through digital dentistry in which scans of patient's mouth (along with impressions and castings thereof) may be used to create a virtual model of the patient's existing mouth; to develop a virtual model of the patient's mouth both pre-dental and post-dental surgery; and to develop a dental surgical plan that connects the two patient-specific virtual models. In this manner, the dental surgical planning can provide for the manufacture of the two respective guides so that the contours of the bone foundation guide body 22 may be created to fit upon the bone 14 of the dental surgical site 12 and as well as properly interact with the contours of the dental implant surgical guide 50 enabling the dental implant surgical guide 50 to fit upon the bone foundation body 22.

Figure 2:
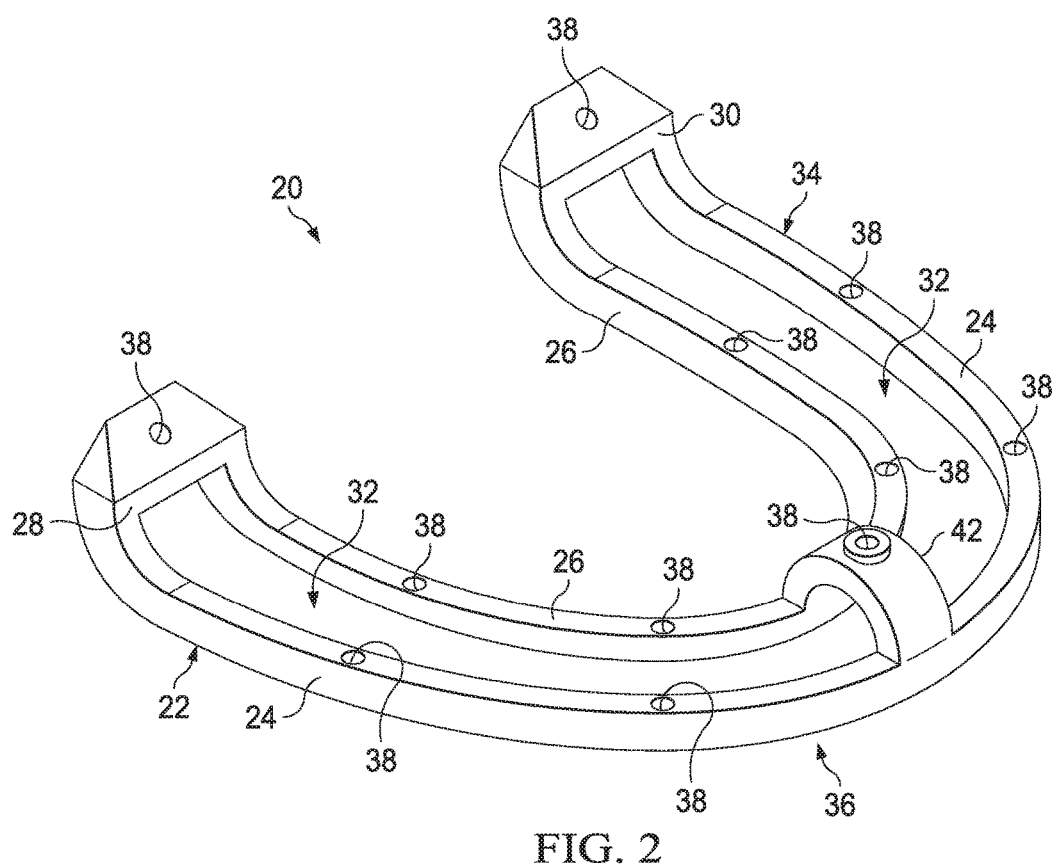
FIG. 2 is a perspective view of one possible embodiment of bone foundation guide of the present invention.

As substantially shown in FIGS. 1 and 2, the bone foundation guide 20, as substantially used by a dental surgeon (not shown) to substantially reduce or augment the bone structure of the dental surgical site 12 as needed for a successful dental surgery, could comprise a bone foundation guide body 22 with a buccal wall 24 and lingual wall 26 connected together at their respective ends by a first end 28 and a second end 30. The first end 28 and the second end 30 could be holding the walls 24, 26 apart from one and other, in a substantially parallel fashion, to generally create and define an open surgical space 32 (e.g., generally passing through the bone foundation guide body 22 to generally continuously connect a portion of the top 34 with a portion of the bottom 36).

The bone foundation guide body 22 may be penetrated by one or more attachment apertures 38 to generally continuously connect the top 34 and bottom 36, although in some embodiments the attachment apertures 38 may be oriented to pass through a buccal 24 wall and/or lingual wall 26. Fasteners 40 may pass through the attachment apertures 38 to substantially anchor into the bone 14 of the dental surgical site 12 (e.g., alveolar ridge) to reversible secure the bone foundation guide body 22 to dental surgical site 12. The attachment aperture 38 could further feature a reinforcement collar (not shown) to support and guide the fastener 40 through the attachment aperture 38.

In some embodiments, the bone foundation guide body 22 may further comprise a first alignment feature such as a bridge 42 that connects the buccal wall 24 with the lingual wall 26 between the first end 38 and the second end 30 and effectively bisecting the open surgical space 32 in some versions of the embodiment. The bridge 42 in such embodiments may also have an attachment aperture 38 penetrating it as well.

Figure 3:
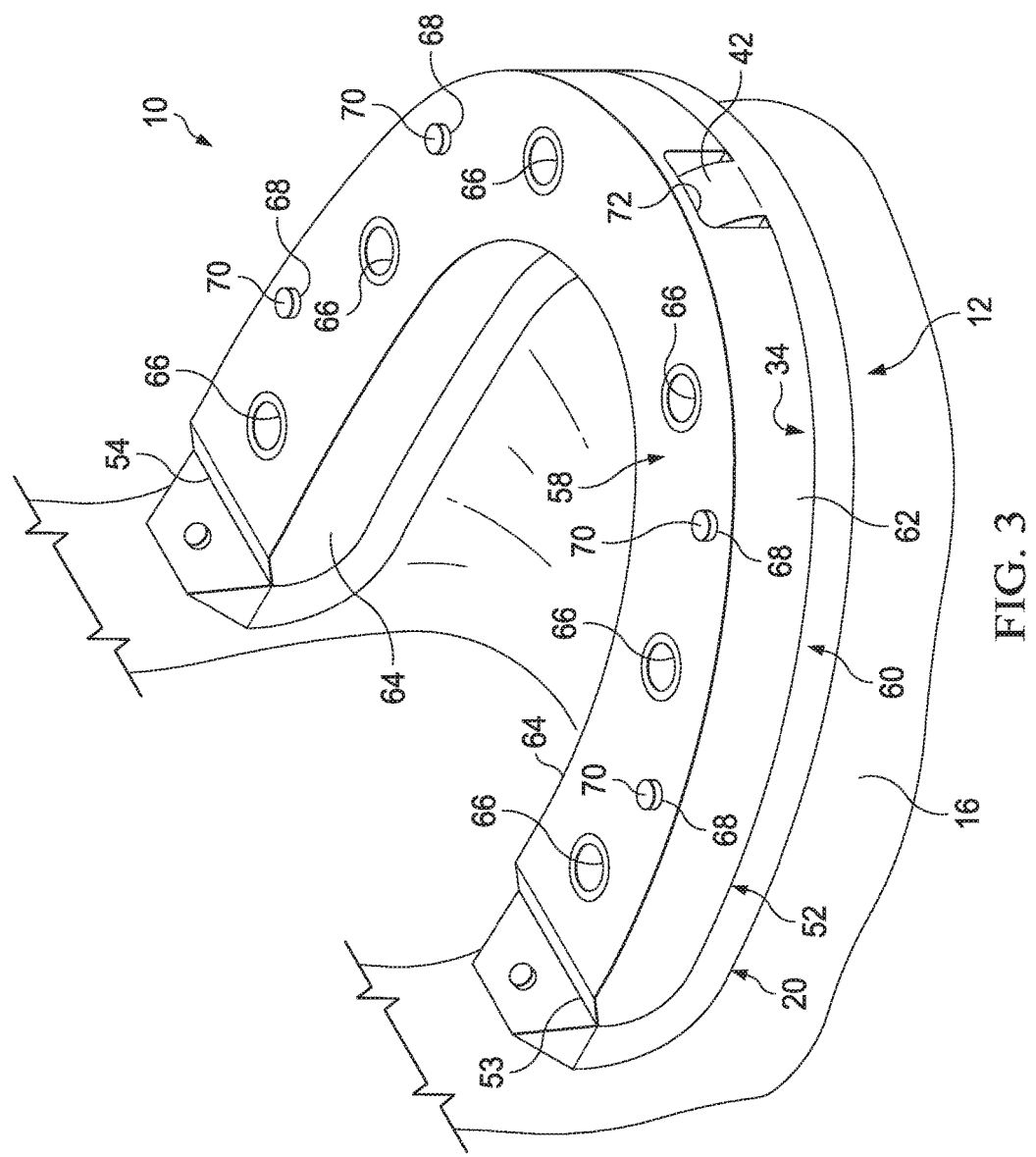
FIG. 3 is substantially a cutaway perspective view of one possible embodiment of the dental implant surgical guide applied to the bone foundation guide.
Figure 4:
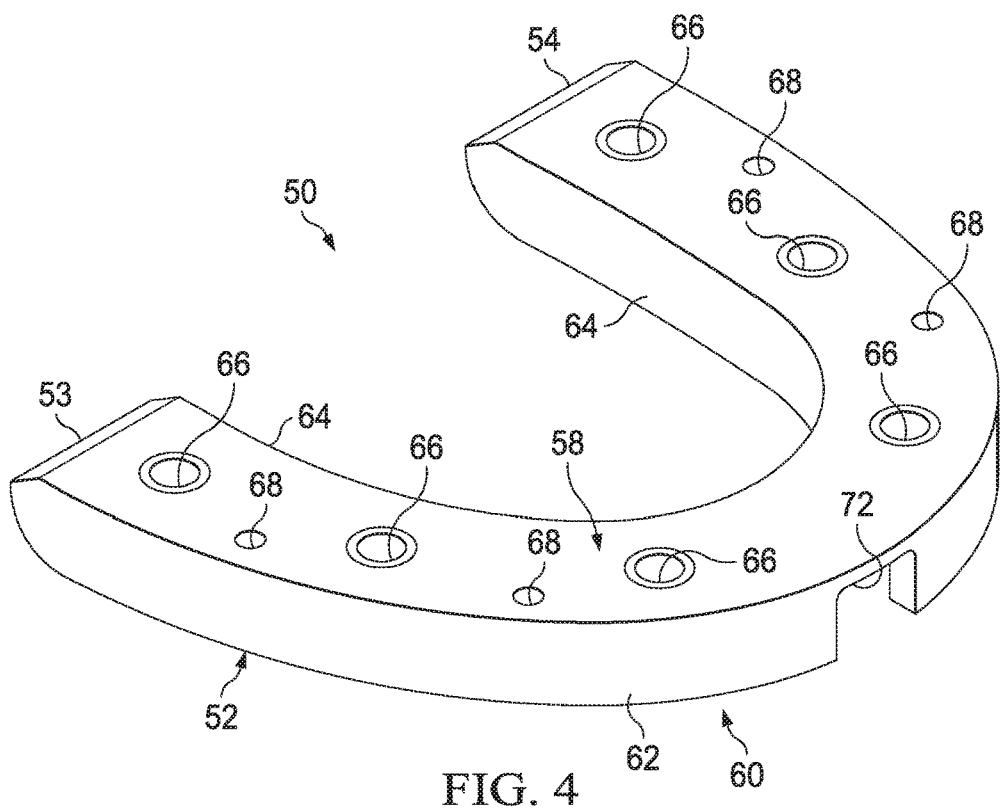
FIG. 4 is substantially a perspective view of one embodiment of the dental implant surgical guide.

As substantially shown in FIGS. 3 and 4, the dental implant surgical guide 50 could be generally used to guide and locate the placement of dental implants in dental surgical site 12. The dental implant surgical guide 50 could comprise a dental implant surgical guide body 52 having a first end side 53 and second end side 54 that terminates the dental surgical guide body 52 and along with a top side 58 and a bottom side 60 that continuously connect a buccal side 62 with a lingual side 64. The bottom side 60 could be designed and/or contoured to receive the top 34 of the bone foundation guide 20 to allow the dental implant surgical guide 50 to be combined with and attached to the bone foundation guide 20.

The dental surgical guide body 52 can be further penetrated by implant apertures 66 that could continuously connect the top side 58 to the bottom side 60 to guide implant preparation and attachment to the dental surgical site 12. The dental surgical guide body 52 could additionally have fastener apertures 68 penetrating the dental surgical guide body 52. The fastener apertures 68 may align up with the respective attachment apertures 38 on the bone foundation guide body 22 so that an extended fastener 70 may pass through both the dental implant surgical guide 50 and the bone foundation guide 20 to attach to the bone 14 relative to the dental surgical site to combine the two guides 20, 50 in place at the dental surgical site 12. In other embodiments, the fastener apertures 68 may align up with respective receptacles in the bone foundation guide body 22 to allow the fasteners 40 passing through the dental surgical guide 20 to anchor into the bone foundation guide body 22 to combine the bone foundation guide 20 with the dental implant guide 50. In this manner, the dental implant surgical guide 50 could: attach directly to the dental surgical site 12; attach to the dental surgical site 12 through the bone foundation guide 20; attach to just the bone foundation guide 20; or combinations thereof.

The bottom side 60 of the dental implant surgical guide 50 can be digitally designed/manufactured to have a contour (e.g., top side 58) that substantially matches the top 34 of the bone foundation guide 20. Conversely, or conjointly, the top 34 of the bone foundation guide body 22 may be digitally designed and created to substantially match and to receive the bottom side 60 of the reciprocal dental surgical guide body 52 to allow the dental implant surgical guide 50 to be mounted to the bone foundation guide 20 so that the bone foundation guide 20 can be joined with the dental implant guide 50 to act as a base for the dental implant surgical guide 50. This conjoining of guides 20, 50 could alleviate the need to remove the bone foundation guide 20 from the dental surgical site 12 prior to attaching the dental implant surgical guide 50 to the dental surgical site 12 as well as alleviate the need to attach the dental implant surgical guide 50 directly to the dental surgical site 12 and the like. In this manner, the dental implant surgical guide 50 generally encloses the open surgical space 32 to allow implants/implant accessories (e.g., implant preparation tools)(not shown) passing though the dental implant surgical guide 50 to be generally pass through an open surgical space 32 of the bone foundation guide 20.

In one possible embodiment, the bottom side 60 of the dental implant surgical guide 50 could have a second alignment feature such as a recess 72 that could accommodate the bone foundation guide's bridge 42. If the bridge 42 was penetrated by an attachment aperture 38, the dental implant surgical guide body 52 could have a respective fastener aperture 68 that could align together to allow passage of the extended fastener 70. Similarly, if an implant aperture 66 penetrated the recess 72 then a suitable aperture or channel could penetrate the bridge 42 to allow implant preparation and attachments to penetrate the bridge 72 as well. In another possible embodiment, the bridge 72 could be cut and removed from the bone foundation guide body 22 so that any implant/implant preparation (e.g., drills, reamers, etc.) could pass unimpeded through that opened-up portion of the open surgical space 32.

Figure 5:
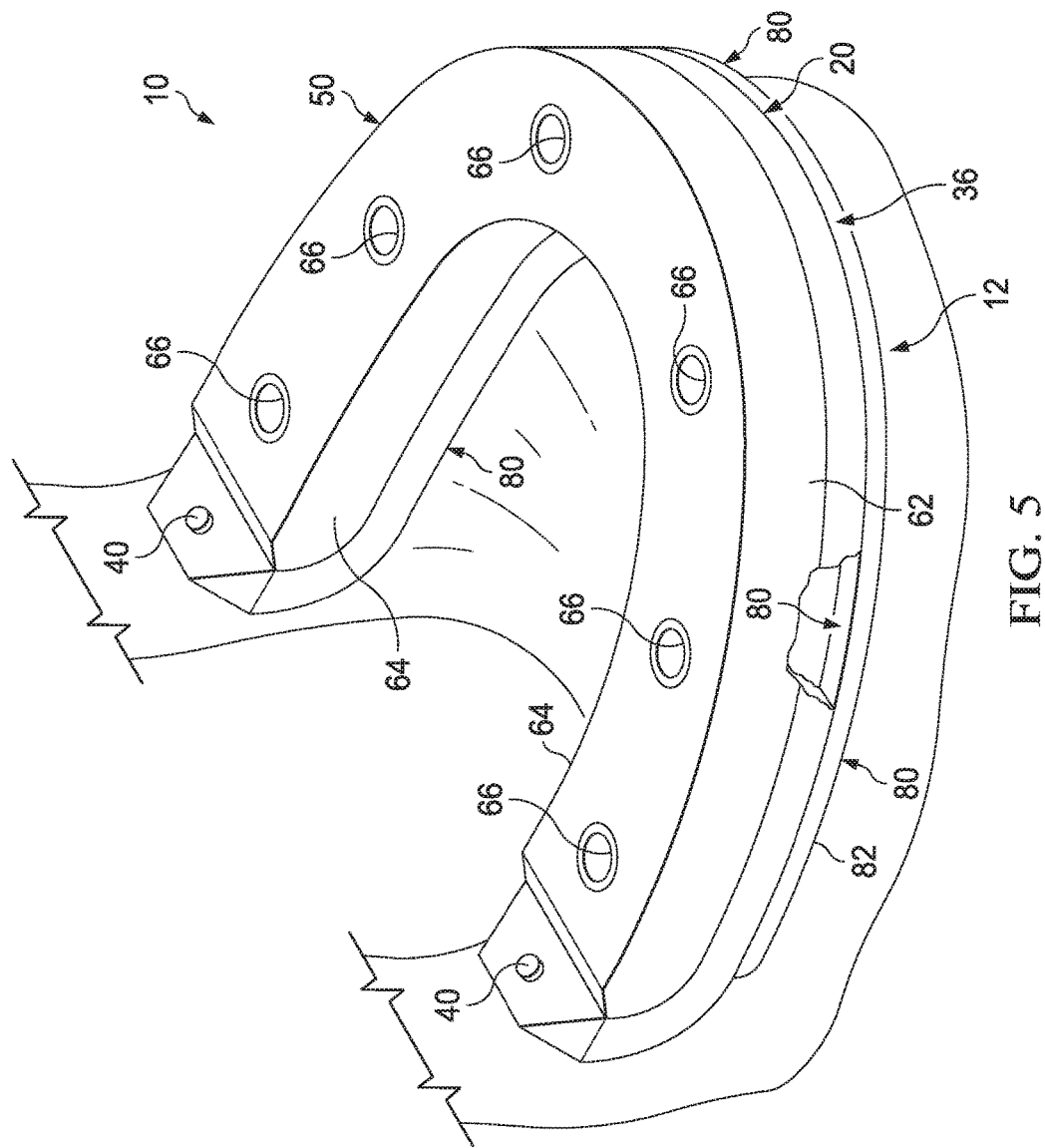
FIG. 5 is substantially a perspective cutaway view of one embodiment of the tissue spacing gasket.

As substantially shown in FIG. 5, one other possible embodiment of the invention 10 could further comprise a tissue spacing gasket 80 that fits between the dental surgical site 12 and the bottom 36 of the bone foundation guide 20. The tissue spacing gasket 80 could be used to set apart the bottom 36 of the bone foundation guide from the dental surgical site 12 to properly replicate the positioning of the dental implant surgical guide 50 (as placed on top 34 of the bone foundation guide 20) as if the gum tissue 16 had been reattached to the surgical (bared bone) site. The thickness of the tissue spacing gasket 80 could be set to the thickness of the gum 16 at that dental surgical site 12 while the gasket bottom 82 can be designed/manufactured to have a contour that matches that of the dental surgical site 12 while the gasket top 84 is contoured to match the bottom 36 of the bone foundation guide 20.

The tissue spacing gasket 80 could be designed and constructed to have a gasket open surgical space that could generally match the footprint of open surgical space 32 of the bone foundation guide 20. Alternatively, the tissue spacing gasket 80 could have individual gasket apertures (not shown) that could be in alignment with the dental implant surgical guide's implant apertures 66. Other versions of the tissue spacing gasket 80 could have additional apertures (not shown) as needed to be in alignment with any fastener apertures/attachment apertures as needed.

Figure 6:
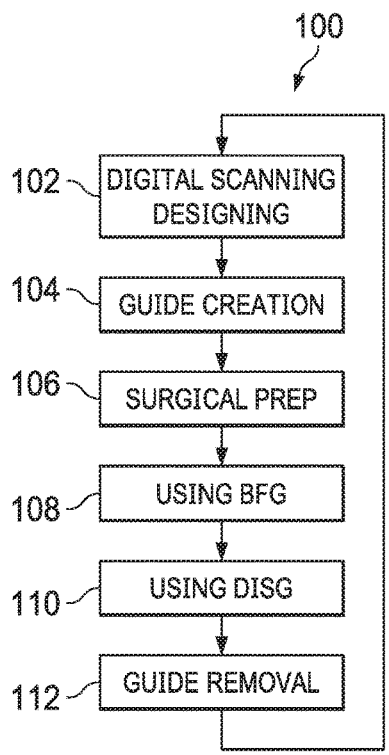
FIG. 6 is substantially a flow schematic showing a method of using the invention.

As substantially shown in FIG. 6, one possible method or process 100 for the use of the invention could start with step 102, digital scanning and modeling for the patient-specific dental surgery. In this step, dental digital methods (digital dentistry) may be used in creating patient-specific map of the patient's mouth (which could include the digital scanning of analogue appliances such as patient specific castings and impressions); in creating models for patient-specific bone remodeling (e.g., foundation and re-contouring) of the upper and/or lower dental arches in the patient's mouth; in creating models for dental implant surgical guides/bone foundation guides and prosthetics used post-patient-specific bone remodeling; in creating a patient specific model of the patient's mouth post dental surgery. After this step is substantially completed, the process 100 could proceed to step 104, creation of the guides and other dental appliances.

In step 104, creation of the guides and other dental appliances, the acquired and processed modeling data can be used to create the patient-specific bone foundation guide and patient-specific dental implant surgical guide that can work in combination as one unit. In this manner, the contours of the bottom side of the dental implant surgical guide can be substantially designed and manufactured generally match the top of the bone foundation guide to allow the two guides to mate together. This mating capability could allow the two guides to come together to form a single apparatus to generally create a dental implant surgical guide that could attach to the bone foundation guide (e.g., as already secured to the dental surgical site). This ability could allow the implant/implant apparatuses being guided through the dental implant surgical guide/the open surgical space to properly interact with the dental surgical site. After this step is substantially completed, the process 100 could proceed to step 106, surgical prep.

In step 106, surgical prep, the dental health care professional could (after properly anesthetizes the patient and instituting other required dental surgical pre-operation protocols) could make incisions in the gum area of the dental surgical site, and peel back the gum to expose the portion of bone being operated upon. After this step is substantially completed, the process 100 could proceed to step 108, use of the bone foundation guide.

In step 108, use of the bone foundation guide, the bone foundation guide is properly placed upon the dental surgical site (e.g., its bottom being contoured to match and receive the exposed bone portion) and properly secured to the site (e.g., fasteners passing through the bone foundation guide to anchor into the bone structure of the dental surgical site). The dental health care professional can then use the bone foundation guide (e.g., BFG) to reduce or augment the bone structure as required utilizing known dental techniques for same to prove the proper bone contour. Once this step is substantially completed, the process 100 could proceed to step 110, use of the dental implant surgical guide.

In step 110, use of the dental implant surgical guide, the dental health care professional could place the bottom side of the dental implant surgical guide upon the top of the bone foundation guide generally enclosing the open surgical space. Fasteners could then penetrate through the surgical guide to embed themselves into the body of the bone foundation guide to secure the surgical guide into place upon the bone foundation guide. In addition or alternatively to this attachment, the fasteners could pass through dental implant surgical guide to directly to secure the surgical guide into place upon the dental surgical site. In addition to or alternatively to this attachment, extended fasteners could penetrate through the both bodies of the bone foundation guide and the dental implant surgical guide and into bone of the dental surgical site.

In one embodiment of the invention, prior to the attachment of the dental implant surgical guide to the bone foundation guide, a tissue spacing gasket may be inserted between the prepared dental surgical site and the bottom of the bone foundation guide. This tissue spacing gasket adjusts the combination for the depth of the gum tissue normally present at the dental surgical site but that has been peeled back at the onset of surgical operations.

The dental healthcare professional could use the two guides combined to substantially direct and operated implant preparation accessories or implements (e.g., drills, reamers, and the like) to properly prepare the dental operation site to receive the implant(s) (e.g., pass through the dental implant surgical guide and into the open surgical space. This preparation could ensure the proper orientation and telemetry of the implant accessories into the bone of the dental surgical site. Once the bone is properly prepared, the implant(s) could then pass through the combination to be anchored into the bone. Once this step is substantially completed, the process 100 could proceed to step 112, removal of the guides.

In step 112, removal of the guides, once the implant(s) is (are) properly located in place within the dental surgical site, the fasteners for the bone foundation guide and/or the dental implant surgical guide could be removed to generally allow the combined guides or the guides individually (as well as any tissue space gasket, if used) to be removed from the dental site.

This process 100 could now allow the attachment of trans mucosal abutment, use of temporary cylinder/associated seal/additional filling methods to properly prepare the dental implant for the attachment of prosthesis and the like. At that time, the dental prosthetics could be checked for fitting upon the placed implant(s). If the prosthetics do not need adjustment, they can be removed from the implant and healing abuts can be fitted in their place as required. The gum tissues can then be sutured or otherwise cover-up the exposed bone to meet up with the abutment/implants. If abutments are not required, then the prosthetic could be placed upon the implants in a secure fashion. If the gum tissues need to heal or need to heal around the healing abutments or the implants require ossification to secure them in place to the bone, then after these event(s) have occurred/or a suitable amount of healing time has passed then the prosthetic could be placed upon the implants in a secure fashion. After this step is substantially completed, the process 100 could proceed back to step 102 as needed.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As shown in the specification, drawings, claims and abstract, the invention provides for the combining together as one unit, a bone foundation guide and a dental implant surgical guide that generally are otherwise used separately. By digitally designing the two guides to be combined together, the time, effort, cost and patient recover time can be reduced for dental implant procedure. In further combining the two guides with a tissue spacing gasket, the combination can now take into account the depth of the tissue that otherwise would be present at the dental surgical site. The guides reversibly combination consequentially properly places and secures a dental implant-retained prosthesis in a manner that reduces patient stress and bruising that may occur if the two guides were applied separately. The designing of the guides (and gasket) to be conjoined to generally allow implant appliances, implants and securing/attachment fasteners to pass through the combination onto the bone at a dental surgical guide.

What is claimed is:

1. A dental system comprising:
   (a) a bone foundation guide configured to guide an alteration of an alveolar ridge, the bone foundation guide comprising a body, wherein the body is configured to be affixed to a bone segment of the alveolar ridge along an entire length of the body, wherein the body comprises:
      (i) a first end of the body, wherein the first end extends vertically,
      (ii) a second end of the body, wherein the second end extends vertically,
      (iii) a buccal wall, wherein the buccal wall extends laterally from the vertically extending first end of the body and the vertically extending second end of the body,
      (iv) a lingual wall, wherein the lingual wall extends laterally from the vertically extending first end of the body and the vertically extending second end of the body,
      (v) a top, and
      (vi) a bottom; and
   (b) a dental implant surgical guide including a dental implant surgical guide body, wherein the dental implant surgical guide body includes two free ends,
      wherein the body of the bone foundation guide is configured to mate with the dental implant surgical guide body with the free ends of the dental implant surgical guide body abutting the vertically extending first end of the body and the vertically extending second end of the body of the bone foundation guide such that the vertically extending first end of the body and the vertically extending second end of the body of the bone foundation guide are positioned proximally relative to the free ends of the dental implant surgical guide body and such that the vertically extending first end of the body and the vertically extending second end of the body of the bone foundation guide are left exposed by the free ends of the dental implant surgical guide body;
   wherein a first side of the vertically extending first end of the body of the bone foundation guide is configured to abut bone while a second side of the vertically extending first end of the body of the bone foundation guide is configured to abut a corresponding one of the free ends of the dental implant surgical guide body,
   wherein a first side of the vertically extending second end of the body of the bone foundation guide is configured to abut bone while a second side of the vertically extending second end of the body of the bone foundation guide is configured to abut a corresponding one of the free ends of the dental implant surgical guide body.

2. The dental system of claim 1, wherein the body of the bone foundation guide further comprises an attachment aperture either passing through at least one of the buccal wall and the lingual wall or passing through the top of the body of the bone foundation guide and the bottom of the body of the bone foundation guide such that the top and the bottom are continuously connected.

3. The dental system of claim 2, wherein the attachment aperture is further configured to receive an alveolar ridge fastener such that the bone foundation guide can be reversibly affixed to the alveolar ridge.

4. The dental system of claim 3 further comprising the alveolar ridge fastener configured to penetrate the attachment aperture.

5. The dental system of claim 1, wherein the body of the bone foundation guide further comprises a bridge configured to connect at least a portion of the buccal wall to at least a portion of the lingual wall.

6. The dental system of claim 1, wherein the extended vertically first end of the body of the bone foundation guide curves relative to the buccal and lingual walls.

7. The dental system of claim 1, wherein the dental implant surgical guide body has a top and a bottom, wherein the bottom of the dental implant surgical guide is configured to couple with the top of the bone foundation guide.

8. The dental system of claim 7, wherein the body of the bone foundation guide is configured to mate with a dental implant surgical guide body such that the first end of the body of the bone foundation guide is configured to extend higher than the top of the dental implant surgical guide body and such that the second end of the body of the bone foundation guide is configured to extend higher than the top of the dental implant surgical guide body.

9. A dental system configured to guide an alteration of an alveolar ridge, the dental system comprising:
(a) a bone foundation guide, the bone foundation guide comprising a body, wherein the body comprises:
  (i) a vertically extending first free proximal end of the body,
  (ii) a vertically extending second free proximal end of the body,
  (iii) a buccal wall extending along a horizontal plane, the vertically extending first free proximal end and the vertically extending second free proximal end each extending vertically relative to the horizontal plane,
  (iv) a lingual wall,
  (v) a top, and
  (vi) a bottom,
  wherein a first end of the buccal wall and a first end of the lingual wall are each connected to the vertically extending first free proximal end of the body,
  wherein a second end of the buccal wall and a second end of the lingual wall are each connected to the vertically extending second free proximal end of the body,
  wherein the body is configured to be affixed to a bone segment of the alveolar ridge along an entire length of the body; and
(b) a dental implant surgical guide, the dental implant surgical guide comprising:
  (i) a dental implant surgical guide body, the dental implant surgical guide body comprising a top side and a bottom side, wherein the body of the bone foundation guide is configured to engage the dental implant surgical guide body, wherein the bottom side of the dental implant surgical guide is configured to couple with the top of the body of the bone foundation guide,
  (ii) a first free proximal end of the dental implant surgical guide body,
  (iii) a second free proximal end of the dental implant surgical guide body, and
  (iv) an implant aperture continuously connecting the top side to the bottom side and configured to receive an implant and guide the implant into the alveolar ridge,
  wherein the dental implant surgical guide is configured to couple with the bone foundation guide such that the first free proximal end of the dental implant surgical guide body is horizontally distal to the vertically extending first free proximal end of the body of the bone foundation guide, and such that the second free proximal end of the dental implant surgical guide body is horizontally distal to the vertically extending second free proximal end of the body of the bone foundation guide;
  wherein the body of the bone foundation guide is configured to mate with the dental implant surgical guide body such that the vertically extending first free proximal end of the body of the bone foundation guide is configured to extend higher than the top side of the dental implant surgical guide body and such that the vertically extending second free proximal end of the body of the bone foundation guide is configured to extend higher than the top side of the dental implant surgical guide body.

10. A dental system configured to guide an alteration of an alveolar ridge, the dental system comprising:
(a) a bone foundation guide, the bone foundation guide comprising a body, wherein the body comprises:
  (i) a first end of the body, wherein the first end extends vertically,
  (ii) a second end of the body, wherein the second end extends vertically,
  (iii) a buccal wall, wherein the buccal wall extends horizontally and distally from the vertically extending first end of the body and the vertically extending second end of the body, and
  (iv) a lingual wall, wherein the lingual wall extends horizontally and distally from the vertically extending first end of the body and the vertically extending second end of the body,
  wherein the body is configured to be affixed to a bone segment of the alveolar ridge along the entire length of the body;
(b) a dental implant surgical guide, the dental implant surgical guide comprising:
  (i) a dental implant surgical guide body, the dental implant surgical guide body comprising a top side and a bottom side,
  wherein the dental implant surgical guide body defines an arc proximally terminating in two free ends that are laterally spaced apart from each other,
  wherein the dental implant surgical guide body is configured to mate with the body of the bone foundation guide with the free ends of the dental implant surgical guide body abutting the vertically extending first end of the body and the vertically extending second end of the body of the bone foundation guide such that the vertically extending first end of the body and the vertically extending second end of the body of the bone foundation guide are positioned proximally relative to the free ends of the dental implant surgical guide body and such that the vertically extending first end of the body and the vertically extending second end of the body of the bone foundation guide leave the free ends of the dental implant surgical guide body exposed, and
  (ii) an implant aperture continuously connecting the top side to the bottom side and configured to receive an implant and guide the implant into the alveolar ridge; and
(c) a tissue spacing gasket, wherein the tissue spacing gasket is configured to be removably affixed to the bone foundation guide.

11. The dental system of claim 10, wherein the body of the bone foundation guide further comprises an attachment aperture passing through the buccal wall and the lingual wall of the body of the bone foundation guide, and
wherein the attachment aperture is further configured to receive a fastener such that the bone foundation guide can be reversibly anchored into the alveolar ridge.

12. The dental system of claim 11, wherein the dental implant surgical guide further comprises a fastener aperture configured to align with the attachment aperture of the body of the bone foundation guide and configured to receive a fastener or extended fastener.

13. The dental system of claim 10, wherein the body of the bone foundation guide further comprises a bridge configured to connect at least a portion of the buccal wall to at least a portion of the lingual wall, and wherein the bottom side of the dental implant surgical guide further comprises a recess configured to accommodate the bridge.

14. The dental system of claim 10, wherein the tissue spacing gasket comprises one or more gasket apertures configured to align with the implant aperture.

* * * * *